United States Patent
Lee et al.

(10) Patent No.: US 9,305,376 B2
(45) Date of Patent: Apr. 5, 2016

(54) MAGNETIC RESONANCE IMAGING APPARATUS AND METHOD OF ACQUIRING FUNCTIONAL IMAGE

(71) Applicant: SAMSUNG ELECTRONICS CO., LTD., Suwon-si (KR)

(72) Inventors: Jun Ki Lee, Suwon-si (KR); Keum Yong Oh, Yongin-si (KR); Praveen Gulaka, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 197 days.

(21) Appl. No.: 13/793,074

(22) Filed: Mar. 11, 2013

(65) Prior Publication Data

US 2014/0133720 A1    May 15, 2014

(30) Foreign Application Priority Data

Nov. 9, 2012  (KR) .......................... 10-2012-0126385

(51) Int. Cl.
| | |
|---|---|
| *G06K 9/00* | (2006.01) |
| *G06T 11/00* | (2006.01) |
| *G01R 33/565* | (2006.01) |
| *A61B 5/00* | (2006.01) |
| *G06T 5/00* | (2006.01) |
| *G06T 5/50* | (2006.01) |
| *G01R 33/48* | (2006.01) |

(52) U.S. Cl.
CPC ............. *G06T 11/003* (2013.01); *A61B 5/0033* (2013.01); *G01R 33/4806* (2013.01); *G01R 33/56509* (2013.01); *G06T 5/003* (2013.01); *G06T 5/50* (2013.01); *G01R 33/4804* (2013.01); *G06T 2207/10076* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 2001/0056231 A1* | 12/2001 | Jesmanowicz et al. ........ | 600/410 |
| 2005/0065421 A1 | 3/2005 | Burckhardt | |
| 2005/0197561 A1 | 9/2005 | Elsinger et al. | |
| 2009/0116761 A1* | 5/2009 | Wheaton et al. ............... | 382/254 |
| 2013/0004038 A1* | 1/2013 | Carmi ........................ | G06T 5/50 382/128 |
| 2013/0188854 A1* | 7/2013 | Bilgic et al. ................... | 382/131 |

(Continued)

FOREIGN PATENT DOCUMENTS

| | | |
|---|---|---|
| EP | 2 130 490 A1 | 12/2009 |
| JP | 7-79943 A | 3/1995 |

(Continued)

OTHER PUBLICATIONS

Catana et al (NPL: "MRI-Assisted PET Motion Correction for Neurologic Studies in an Integrated MR-PET Scanner", Journal of Nuclear Medince, 2011; vol. 52:154-161).*

(Continued)

*Primary Examiner* — Bhavesh Mehta
*Assistant Examiner* — Oneal R Mistry
(74) *Attorney, Agent, or Firm* — Sughrue Mion, PLLC

(57) ABSTRACT

A method of acquiring a functional image whose artifacts due to a motion of an object are corrected includes acquiring functional image data of an object, acquiring structural image data of the object, acquiring motion information of the object based on the structural image data, correcting the functional image data based on the motion information related to motion of the object, and obtaining a functional image of the object.

24 Claims, 23 Drawing Sheets

(56) References Cited

U.S. PATENT DOCUMENTS

2013/0279786 A1* 10/2013 Lin et al. .................. 382/131
2014/0121498 A1* 5/2014 Hubbard .................. 600/419

FOREIGN PATENT DOCUMENTS

KR   10-2009-0113494 A   11/2009
WO   2012/037181 A1   3/2012

OTHER PUBLICATIONS

Tahmasebi et al (NPL: Is the Link between Anatomical Structure and Function Equally Strong at All Cognitive Levels of Processing?, Cerebral Cortex Advance Access published Sep. 5, 2011, pp. 11).*

Communication dated Feb. 25, 2014 issued by the European Patent Office in counterpart European Patent Application No. 13190069.8.
Communication, dated Nov. 27, 2013, issued by the Korean Intellectual Property Office in counterpart Korean Patent Application No. 10-2012-0126385.
International Search Report (PCT/ISA/210), dated Jan. 29, 2014, issued by the International Searching Authority in counterpart International Patent Application No. PCT/KR2013/010072.
Communication dated Mar. 11, 2015 issued by the European Patent Office in counterpart European Patent Application No. 13 190 069.8.
Klaus Mathiak et al.; "Evaluation of Motion and Realignment for Functional Magnetic Resonance Imaging in Real Time"; Magnetic Resonance in Medicine; vol. 45; 2001; pp. 167-171.

* cited by examiner

FIG. 9A
FIG. 9B
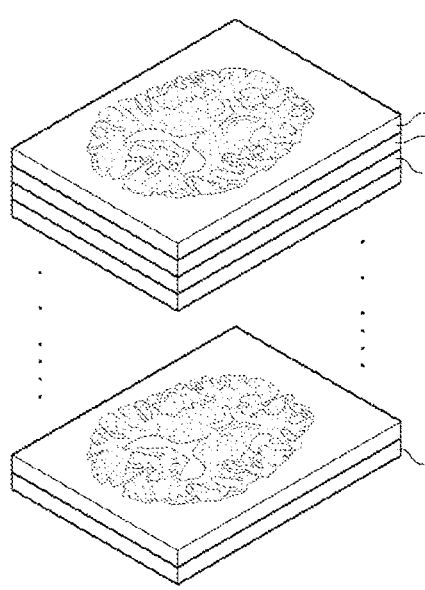
< fMRI volume data >
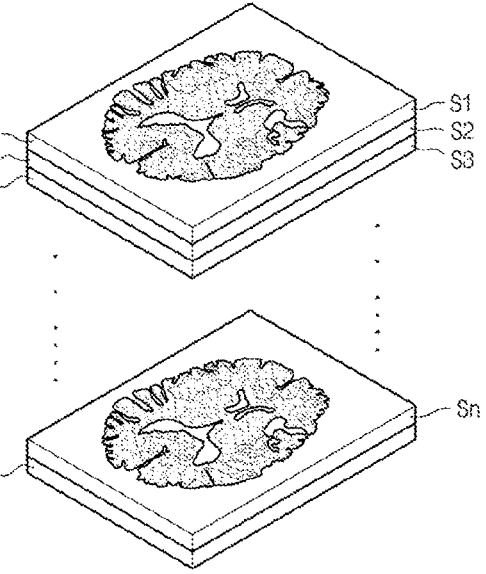
< sMRI volume data >

MAGNETIC RESONANCE IMAGING APPARATUS AND METHOD OF ACQUIRING FUNCTIONAL IMAGE

CROSS-REFERENCE TO RELATED APPLICATION

This application claims the priority from Korean Patent Application No. 10-2012-0126385, filed on Nov. 9, 2012 in the Korean Intellectual Property Office, the disclosure of which is incorporated herein by reference in its entirety.

BACKGROUND

1. Field

Apparatuses and methods consistent with exemplary embodiments relate to a magnetic resonance imaging (MRI) apparatus used to diagnose various diseases using magnetic resonance (MR) images and a method of acquiring a functional image using the same.

2. Description of the Related Art

MRI apparatus generates images representing the density of atomic nuclei and physical and chemical properties by causing nuclear magnetic resonance of hydrogen atomic nuclei in the body using radio frequencies (RF) as specific ionization radiation and magnetic fields that are not harmful to humans.

MRI apparatuses are used to diagnose the patients by applying a predetermined frequency and energy to atomic nuclei under influence of a predetermined range of a magnetic field and converting energy emitted from the atomic nuclei into signals.

A proton is a constituent of an atomic nucleus and has a spin angular momentum and magnetic dipoles. Therefore, atomic nuclei are aligned in the direction of a magnetic field applied thereto and perform precession in the direction of the magnetic field. Thus, an image of a human body may be acquired via nuclear magnetic resonance.

Although MRI apparatuses are widely used to image the anatomical structure of a human and diagnose diseases, in recent years, attempts to form images representing functions of body organs, in particular functions of the brain, have been made. A representative example is functional MRI (fMRI).

The specific areas of the brain have specific functions, and consequently local cerebral blood flow and metabolism of the areas may increase when performing the specific functions. Functional MRI induces local nerve activation of the brain using such physiological variation, and thereafter represents a position of a corresponding function as an image. Functional MRI may exhibit more superior space and time resolution than positron emission tomography (PET), and may be repeatedly executed because injection of an isotope is not required.

Although there are various functional MRI methods, a blood oxygen level-dependent (BOLD) method is the most widely used. Local blood flow increase caused by activation of the brain means an increased amount of oxygen supplied to activated brain tissues. In this case, the increased supply of oxygen increases the amount of oxyhemoglobin in capillaries and veins, causing a reduction in the density of deoxyhemoglobin. Since deoxyhemoglobin is a paramagnetic material that reduces a T2 relaxation time of the surrounding area, a reduction in this material causes an increase of signals in a T2 weighted image.

However, if motion of a patient occurs during scanning for functional MRI, images representing functions, i.e., functional images acquired by a functional MRI, may have artifacts. Although the correction of such artifacts has been carried out via image processing, such as registration of the functional images, the functional images provide insufficient anatomical information for accurate correction of artifacts caused by patient motion.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to one or more of exemplary embodiments, there is provided a method of acquiring a functional image, including acquiring both structural image data and functional image data, recognizing motion of an object using the structural image data, and acquiring a functional image whose artifacts due to motion of the object are corrected by correcting the functional image data based on the recognized motion of the object.

In accordance with an aspect of an exemplary embodiment, there is provided a method of acquiring a functional image using an MRI apparatus, the method includes acquiring functional image data with respect to an object, acquiring structural image data with respect to the object, acquiring information related to motion of the object based on the structural image data, and correcting the functional image data based on the information related to motion of the object, to acquire a functional image with respect to the object.

The functional image may include a brain functional image, a metabolism functional image, a temperature image, and a spectroscopic image.

Acquiring the structural image data with respect to the object may include acquiring the structural image data at a predefined time interval.

The structural image data with respect to the object may include acquiring the structural image data between acquisitions of the respective functional image data.

The functional image data and the structural image data may include slice image data with respect to the object.

The functional image data and the structural image data may include volume image data with respect to the object.

Acquiring the structural image data with respect to the object may include acquiring the structural image data in each of an activation section and a deactivation section of a function of interest to be confirmed.

Acquiring the structural image data with respect to the object may include forming a k-space by sampling an echo signal of the object via compressed sensing, and acquiring the structural image data from the k-space.

Acquiring the structural image data with respect to the object may include forming a k-space by sampling a low-frequency region of an echo signal of the object, and acquiring the structural image data from the k-space.

Acquiring the information related to motion of the object based on the structural image data may include registering the structural image data, and calculating a transformation matrix used in registration of the structural image data.

Correcting the functional image data based on the information related to motion of the object to acquire the functional image with respect to the object may include acquiring a functional image whose artifacts due to motion of the object are corrected by registering the functional image data based on the transformation matrix.

In accordance with another aspect of an exemplary embodiment, an MRI apparatus includes an image processor that acquires functional image data and structural image data with respect to an object, acquires information related to motion of the object based on the structural image data, and corrects the functional image data based on the information related to motion of the object, to acquire a functional image with respect to the object, and a display that displays the functional image.

The functional image may include a brain functional image, a metabolism functional image, a temperature image, and a spectroscopic image.

The image processor may acquire the structural image data at a predefined time interval.

The image processor may acquire the structural image data between acquisitions of the respective functional image data.

The functional image data and the structural image data may include slice image data with respect to the object.

The functional image data and the structural image data may include volume image data with respect to the object.

The image processor may acquire the structural image data in each of an activation section and a deactivation section of a function of interest to be confirmed.

The image processor may form a k-space by sampling an echo signal of the object via compressed sensing, and may acquire the structural image data from the k-space.

The image processor may form a k-space by sampling a low-frequency region of an echo signal of the object, and may acquire the structural image data from the k-space.

The image processor may register the structural image data to thereby calculate a transformation matrix used in registration of the structural image data, and may acquire a functional image whose artifacts due to motion of the object are corrected by registering the functional image data based on the transformation matrix.

BRIEF DESCRIPTION OF THE DRAWINGS

The above and/or other aspects will become apparent by describing certain exemplary embodiments, with reference to the accompanying drawings, in which:

FIGS. 9A and 9B are views conceptually illustrating a method of acquiring structural image data of an object in relation to acquisition of functional image data, according to an exemplary embodiment;

DETAILED DESCRIPTION

Figure 1:
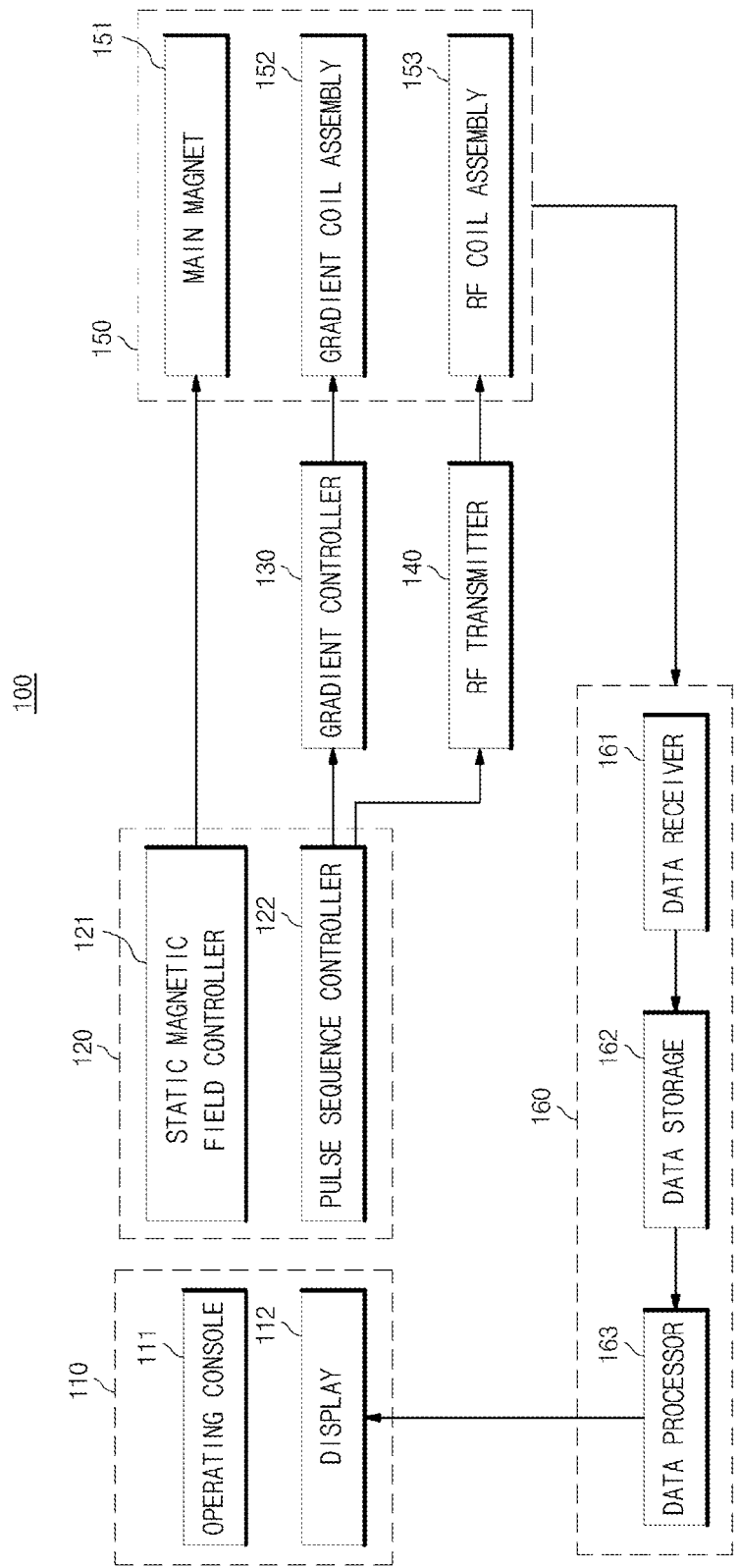
FIG. 1 is a control block diagram of an MRI apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a control block diagram of an MRI apparatus according to an exemplary embodiment.

Referring to FIG. 1, the MRI apparatus 100 according to an exemplary embodiment includes a magnet assembly 150 to generate a magnetic field and cause resonance of atomic nuclei, a controller 120 to control operations of coils of the magnet assembly 150, an image processor 160 to form an MR image upon receiving echo-signals generated from the atomic nuclei, and a workstation 110 to control operations of the MRI apparatus 100.

The magnet assembly 150 includes a main magnet 151 to generate a static magnetic field in the magnet assembly 150, a gradient coil assembly 152, i.e., gradient coils, to generate a gradient in the static magnetic field, and an RF coil assembly 153 to excite atomic nuclei by applying an RF pulse and receive echo signals from the atomic nuclei.

The controller 120 includes a static magnetic field controller 121 to control the strength and direction of the static magnetic field generated by the main magnet 151, and a pulse sequence controller 122 to generate a pulse sequence to control the gradient coil assembly 152 and the RF coil assembly 153.

The MRI apparatus 100 according to an exemplary embodiment may include a gradient controller 130 to apply a gradient signal to the gradient coil assembly 152, and an RF transmitter 140 to apply an RF signal to the RF coil assembly 153.

As the gradient controller 130 and the RF transmitter 140 are controlled by the pulse sequence controller 122, the magnetic field gradient generated in the static magnetic field and the RF pulse applied to the atomic nuclei may be adjusted.

The MRI apparatus according to an exemplary embodiment includes the workstation 110 to allow an operator of the MRI apparatus 100 to manipulate equipment, by entering control commands related to the operations of the MRI apparatus 100.

The workstation 110 may include an operating console 111 to assist the operator in manipulating a system, and a display 112 to display a control state and an image formed by the image processor 160 to assist a user in diagnosing the physical condition of an imaged object 200.

Figure 2:
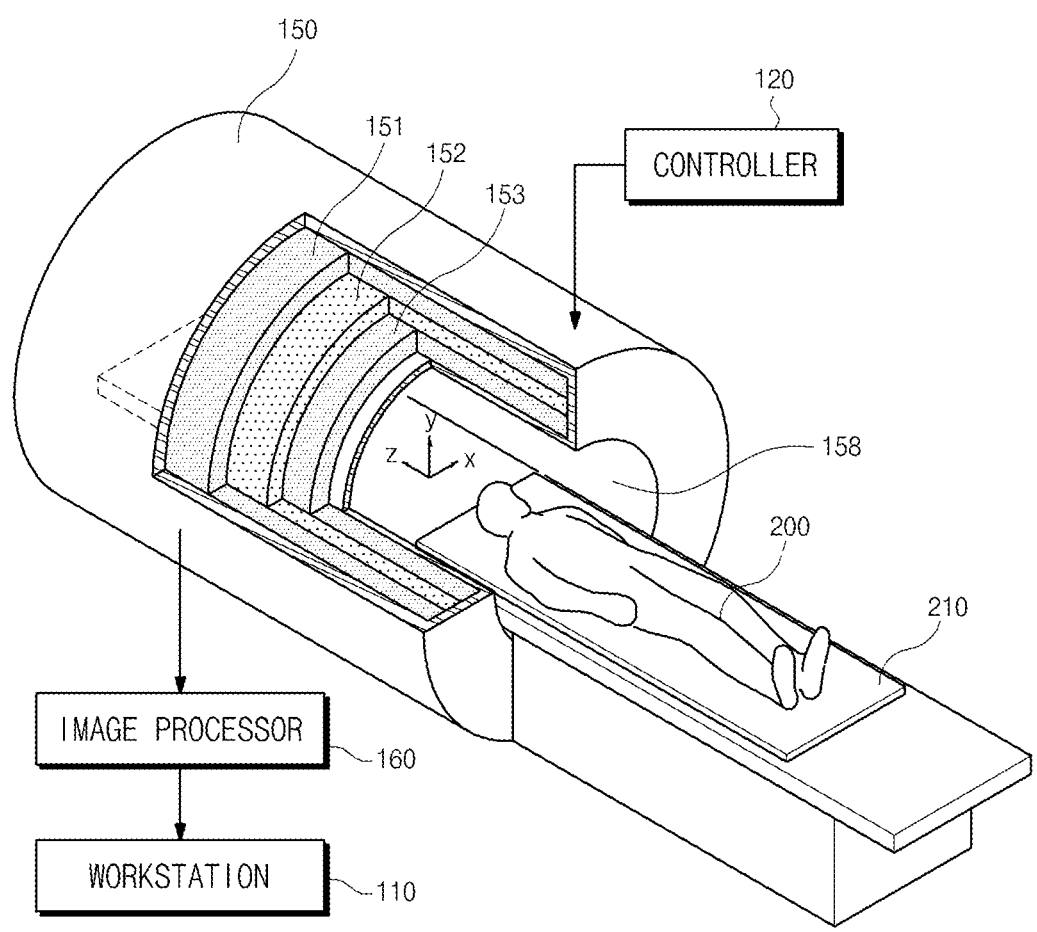
FIG. 2 is an overall view of the MRI apparatus according to an exemplary embodiment.
Figure 3:
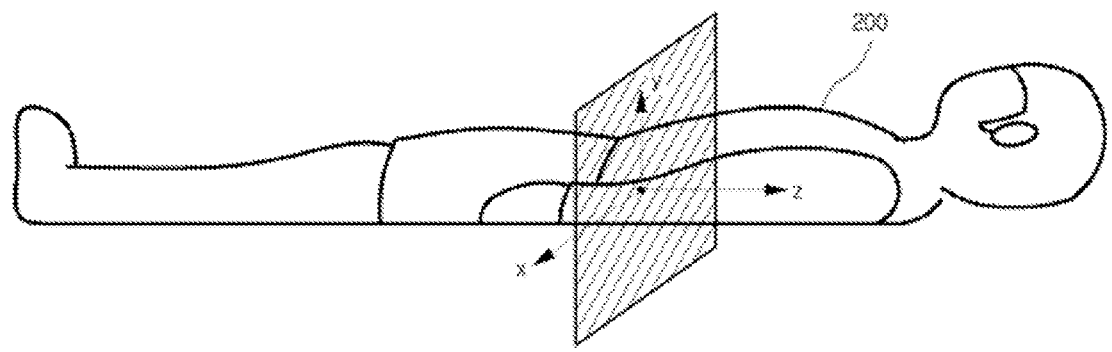
FIG. 3 is a view illustrating a space, in which an object is placed, based on X, Y, and Z axes.
Figure 4A:
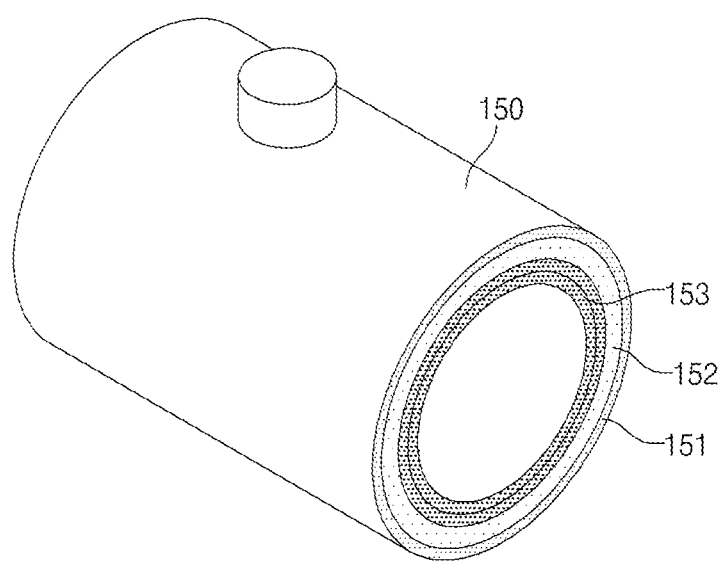
FIGS. 4A and 4B are views illustrating configurations of a magnet assembly and a gradient coil assembly.
Figure 4B:
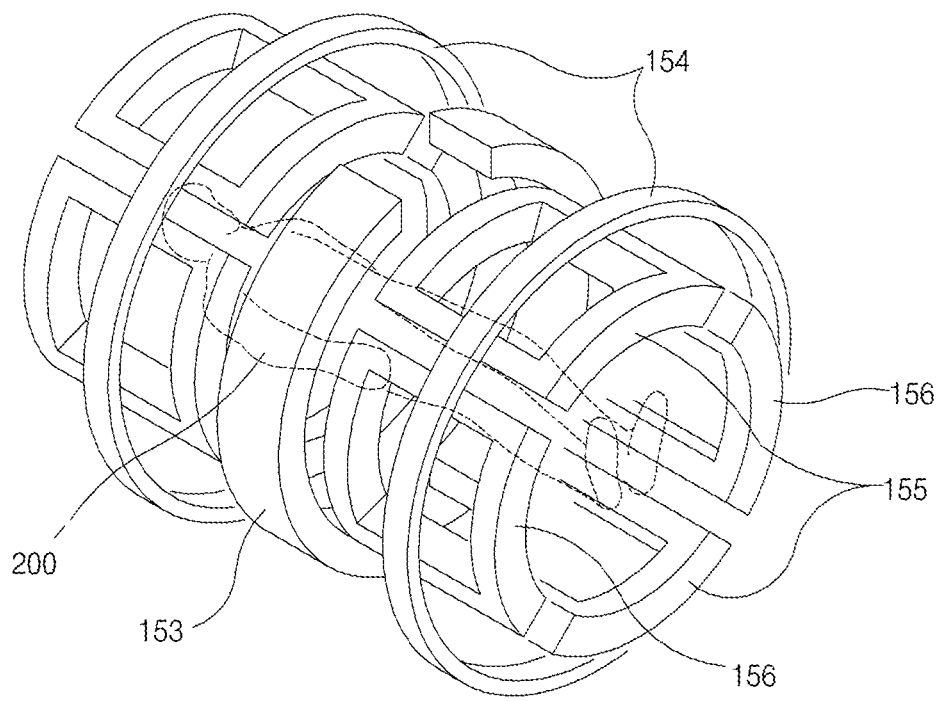
Figure 5:
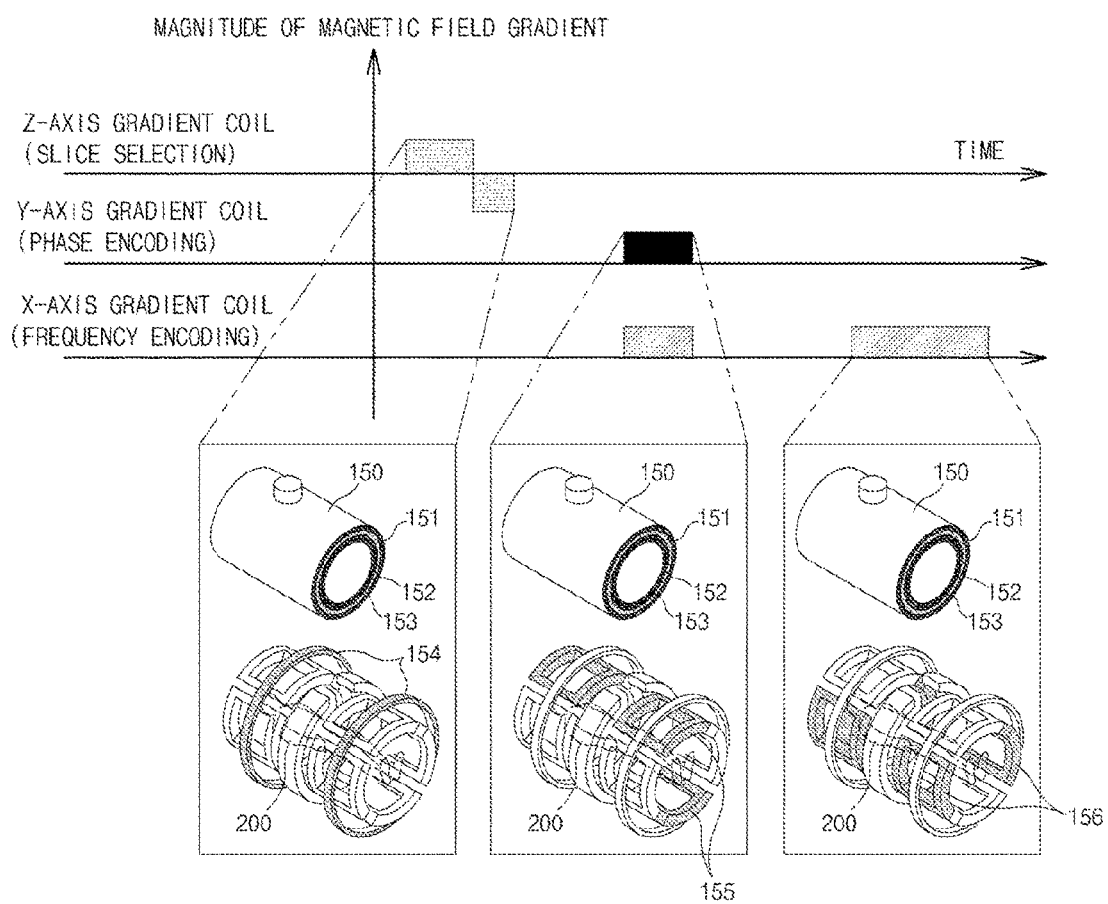
FIG. 5 is a view illustrating gradient coils of the gradient coil assembly and pulse sequences related to operations of the respective gradient coils.

FIG. 2 is an overall view of the MRI apparatus 100, and FIG. 3 is a view showing a cross-section of an examination region, i.e., imaging region, in which an object 200 to be imaged is placed, based on X, Y, and Z axes. FIGS. 4A and 4B are views illustrating configurations of the magnet assembly and the gradient coil assembly, and FIG. 5 is a view illustrating gradient coils of the gradient coil assembly and pulse sequences related to operations of the respective gradient coils.

A detailed operation of the MRI apparatus according to an exemplary embodiment is described below with reference to FIGS. 1 to 5.

The magnet assembly 150 is formed as a cylinder having an empty interior space, such as a cavity or a bore 158, which corresponds to the examination region.

A transfer unit 210 may be provided to transfer the object 200 into the bore 158 to obtain an MR signal.

The magnet assembly 150 includes the main magnet 151, the gradient coil assembly 152, and the RF coil assembly 153.

The main magnet 151 may include coils wound around the bore 158. When the current is applied to the main magnet 151, a static magnetic field $B_0$ is generated in the bore 158, i.e., the examination region.

The direction of the magnetic field may be parallel to a Z axis of the magnet assembly 150.

The static magnetic field generated in the bore 158 causes atoms of the object 200, more particularly, atomic nuclei of hydrogen atoms to be aligned, in the direction of the static magnetic field and to perform precession about the direction of the static magnetic field. Precession speed of atomic nuclei is determined by a precession frequency, i.e., Larmor frequency, which is represented by the following Equation 1.

$$\omega = \gamma B_0, \qquad \text{Equation 1}$$

where $\omega$ is a precession frequency, $\gamma$ is a proportional constant, and $B_0$ is the strength of a magnetic field which is measured in tesla (T) or gauss (G).

The proportional constant $\gamma$ is different for each kind of atomic nuclei.

For example, a hydrogen proton has a precession frequency of 42.58 MHz in the magnetic field having the strength of 1 T. Since hydrogen accounts for the greatest number of atoms of the human body, MRI apparatus may acquire an MR signal using precession of hydrogen protons.

The gradient coil assembly 152 generates a magnetic field gradient by applying a gradient to the static magnetic field generated in the bore 158.

As illustrated in FIG. 3, a Z axis is parallel to a longitudinal direction extending from the feet to the head of the object 200 and parallel to the direction of the static magnetic field, an X axis is parallel to a lateral direction of the object 200, and a Y axis is parallel to a vertical direction of a diameter of the bore 158.

To acquire three-dimensional (3D) spatial information, magnetic field gradients in the X, Y, and Z axes may be generated. Thus, the gradient coil assembly 152 includes three pairs of gradient coils.

As illustrated in FIGS. 4 and 5, Z-axis gradient coils 154 are formed as a pair of ring-shaped coils, Y-axis gradient coils 155 are located above and below the object 200, and X-axis gradient coils 156 are located at left and right sides of the object 200.

If direct current having opposite polarities is applied in opposite directions to the two Z-axis gradient coils 154, variation of a magnetic field occurs in the Z-axis direction, causing generation of a magnetic field gradient. FIG. 5 illustrates generation of the Z-axis magnetic field gradient during operation of the Z-axis gradient coils 154, by using pulse sequences.

The Z-axis gradient coils 154 are used to select a slice. As the gradient of the Z-axis magnetic field increases, a thinner slice may be selected.

When a slice is selected via the magnetic field gradient generated by the Z-axis gradient coils 154, all of the spins of the slice have the same frequency and the same phase, and may be indistinguishable from one another.

Thus, a magnetic field gradient is generated in the Y-axis direction by the Y-axis gradient coils 155, which causes a phase shift such that the lines of the slice have different phases.

That is, once the Y-axis magnetic field gradient has been generated, the spins of the line, to which the higher strength of the magnetic field gradient is applied, undergo phase variation at a high frequency, and the spins of the line, to which the lower strength of the magnetic field gradient is applied, undergo phase variation at a low frequency.

After the Y-axis magnetic field gradient disappears, the respective lines of the selected slice have different phases due to a phase shift, which enables distinction between the respective lines. As such, the magnetic field gradient generated by the Y-axis gradient coils 155 is used for phase encoding.

FIG. 5 illustrates generation of the Y-axis magnetic field gradient during operation of the Y-axis gradient coils 155, by using pulse sequences.

Thus, selection of the slice is performed according to the magnetic field gradient generated by the Z-axis gradient coils 154, and phase distinction of the lines of the selected slice is perform by the magnetic field gradient generated by the Y-axis gradient coils 155. However, the respective spins of each line have the same frequency and the same phase, and may be indistinguishable from one another.

Accordingly, a magnetic field gradient is generated in the X-axis direction by the X-axis gradient coils 156, which causes the respective spins of each line to have different frequencies, which enables distinction between the respective spins.

As such, the magnetic field gradient generated by the X-axis gradient coils 156 is used for frequency encoding.

As described above, the magnetic field gradients generated by the Z, Y, and X axes gradient coils realize spatial encoding to encode spatial positions of the respective spins via slice selection, phase encoding, and frequency encoding.

The gradient coil assembly 152 is connected to the gradient controller 130, which applies a drive signal to the gradient coil assembly 152 in response to a control signal transmitted from the pulse sequence controller 122, to enable generation of the magnetic field gradients.

The gradient controller 130 may include three driving circuits corresponding to the three pairs of gradient coils 154, 155 and 156 of the gradient coil assembly 152.

As described above, atomic nuclei aligned by a magnetic field perform precession at a Larmor frequency. A magnetization vector sum of multiple atomic nuclei may be designated by a single net magnetization M.

A Z-axis component of the net magnetization is not measured and only $M_{xy}$ is detectable. Thus, to acquire an MR signal, atomic nuclei is excited so that the net magnetization is present over an XY plane. For excitation of atomic nuclei, an RF pulse tuned to a Larmor frequency may be applied to the static magnetic field.

The RF coil assembly 153 includes a transmit coil to transmit an RF pulse and a receive coil to receive electromagnetic waves emitted from the excited atomic nuclei, i.e., an MR signal.

The RF coil assembly 153 is connected to the RF transmitter 140, and the RF transmitter 140 applies a drive signal to the RF coil assembly 153 in response to a control signal transmitted from the pulse sequence controller 122 to enable transmission of the RF pulse.

The RF transmitter 140 may include a modulator circuit to modulate an output signal into an RF pulse signal, and an RF power amplifier to amplify the RF pulse signal.

The RF coil assembly 153 is also connected to the image processor 160. The image processor 160 includes a data receiver 161 to receive the MR signal from the RF coil assembly 153 and generate data for formation of an MR image, and a data processor 163 to form an MR image by processing the received data.

The data receiver 161 includes a preamplifier to amplify the MR signal received by the receive coil of the RF coil assembly 153, a phase detector to detect a phase of the MR signal received from the preamplifier, and an analog-to-digital (A/D) converter to convert an analog signal acquired by the phase detector into a digital signal. The data receiver 161 transmits the digitized MR signal to a data storage 162.

The data storage 162 has a data space defined as a two-dimensional (2D) Fourier space. When all of the scanned data is stored in the data storage 162, the data processor 163 performs 2D inverse Fourier transform on the data within the 2D Fourier space to reconstruct an image of the object 200. The reconstructed image is displayed on the display 112.

A spin echo pulse sequence may be used to acquire an MR signal from atomic nuclei. When the RF coil assembly 153 sequentially applies a first RF pulse and a second RF pulse with an appropriate time interval Δt therebetween, the atomic nuclei show strong transverse magnetization after a time Δt lapses after application of the second RF pulse, which enables acquisition of an MR signal.

This method is referred to as a spin echo pulse sequence, and the time between the application of the first RF pulse and generation of the MR signal is called time echo (TE).

A flip angle of protons may be represented as 90° RF pulse, 180° RF pulse, or the like based on the flip degree with respect to an axis where the protons are located before being flipped.

However, if motion of a patient occurs during scanning for functional MRI, a functional image acquired by functional MRI may have artifacts.

The brain does substantially not vary in shape during scanning, and the entire shape shows only translation in any one direction of upper and lower and left and right directions or rotation by motion of a patient.

Figure 6:
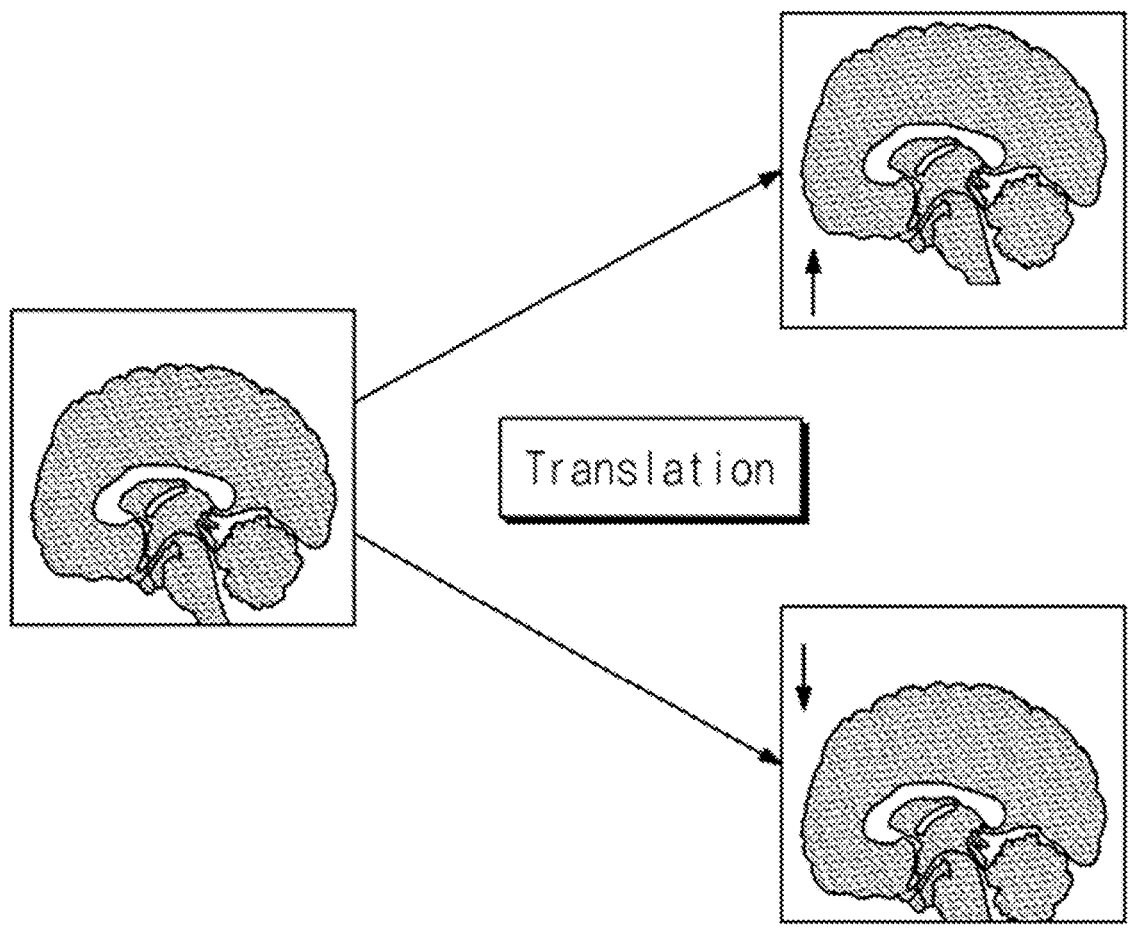
FIGS. 6, 7, and 8 are views conceptually illustrating movement of a functional image depending on motion of an object.
Figure 7:
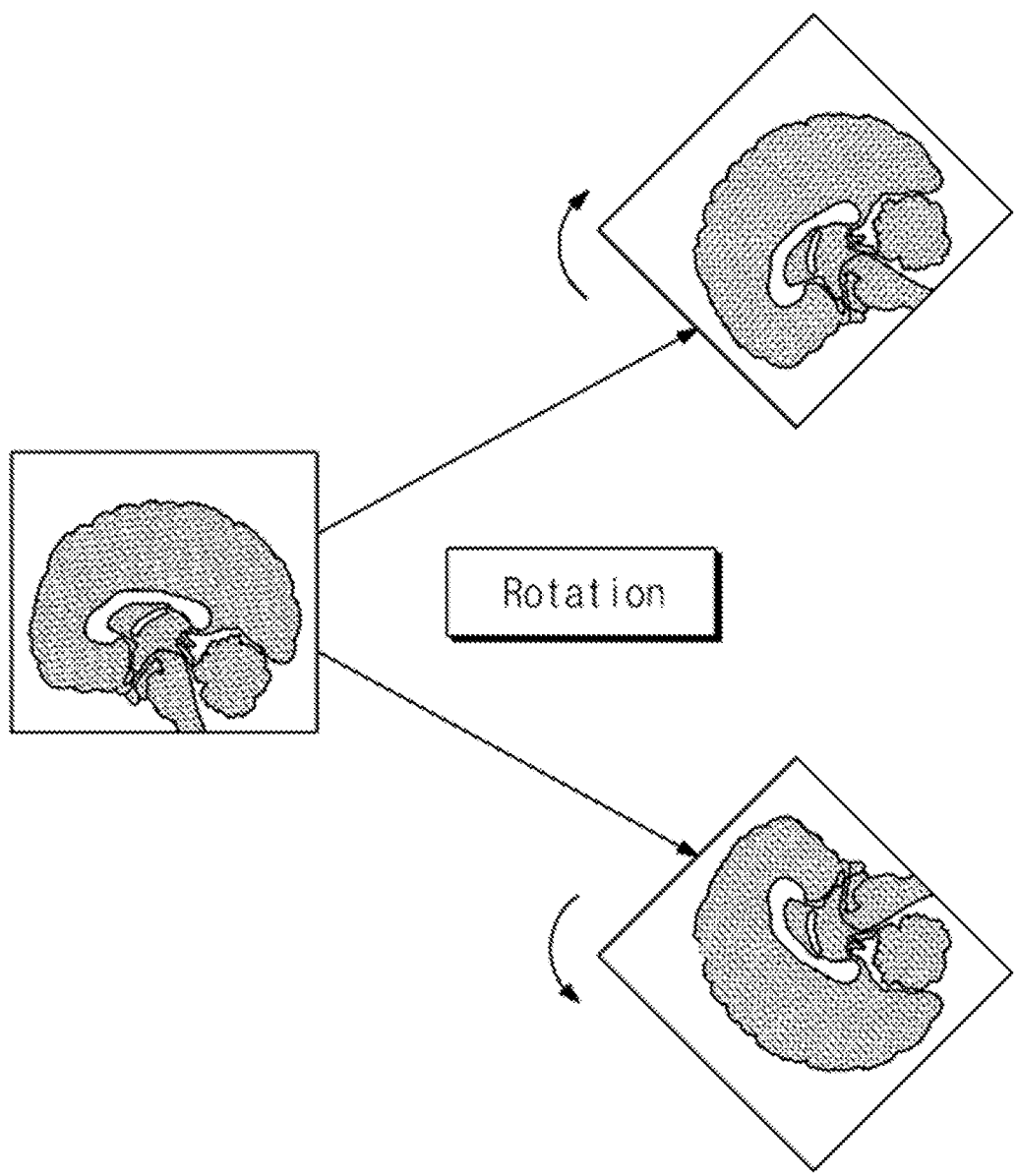
Figure 8:
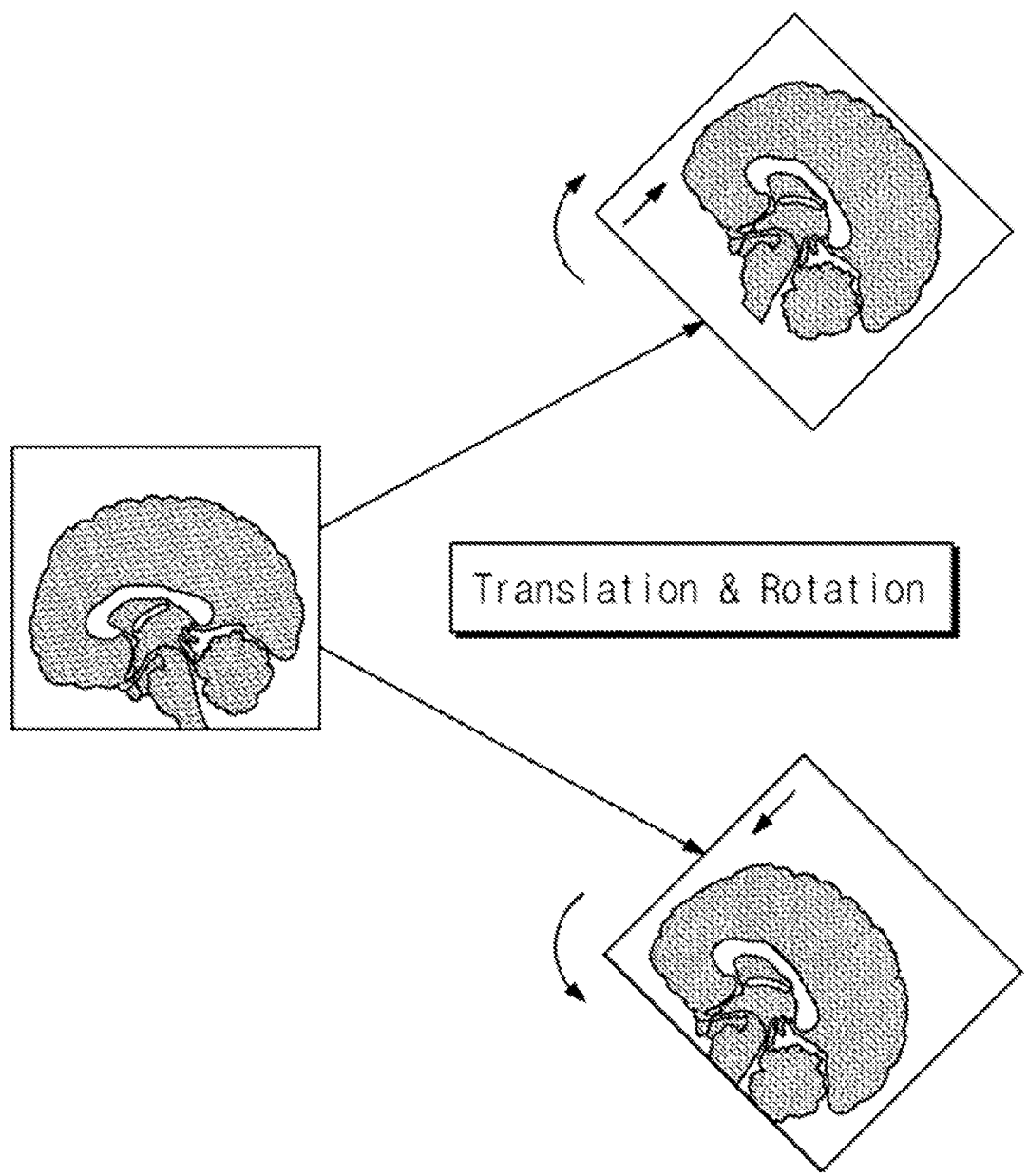

FIGS. 6 to 8 are views conceptually illustrating movement of a functional image depending on motion of an object.

With motion of the object, as illustrated in FIG. 6, an image of the brain, which has undergone upward or downward translation as compared to an image when no motion of the object occurs, is acquired.

As illustrated in FIG. 7, an image of the brain, which has undergone rotation by motion of a patient as compared to an image when no motion of the object occurs, may be acquired.

As illustrated in FIG. 8, an image of the brain, which has undergone translation and rotation by motion of a patient as compared to an image when no motion of the object occurs, may be acquired.

A series of functional image data, which have undergone translation or rotation by motion of a patient during scanning, may be subjected to correction of effects of translation and rotation due to motion of the object via registration.

Rigid body registration may be used as registration of functional image data. Rigid body registration is image registration using only translation and rotation of images under the assumption that there occurs no deformation or distortion of an anatomical area of interest. Since the brain has no temporal deformation as compared, for example, to the heart or the lungs that deform temporarily because of the heartbeat and breathing, functional image data of the brain may be subjected to rigid body registration.

However, functional image data acquired by functional MRI may contain artifacts, such as geometric distortion, intensity non-uniformity, and the like, and may be unsuitable for correction of effects due to the motion of an object based on anatomical information. Also, the functional image data is focused on functional analysis to measure variation in blood flow rather than anatomical information, and, therefore, may be unsuitable for registration based on anatomical information.

An exemplary embodiment proposes a method of acquiring a functional image by using structural image data that shows an anatomical structure of a scan of the object for data registration for motion correction of functional image data. Although, in an exemplary embodiment, the acquisition of the functional MR images of the brain is described in detail, this is only an example. An exemplary embodiment is not limited to the functional imaging of the brain, and may be applicable to metabolism functional images, temperature images, pain representing images, spectroscopic images, and the like.

Temperature images are acquired via an imaging method that monitors a temperature of an object using a sequence to determine temperature variation, and may be utilized in treatments using High Intensity Focused Ultrasound (HIFU). Metabolism functional images are acquired via an imaging method that monitors the density of a metabolism material, such as sodium, phosphorus, carbon, ATP, and the like. Spectroscopic images are acquired via an imaging method that monitors information on the density of a chemical material within a voxel that constitutes an image.

Accordingly, a method of acquiring a functional image by correcting effects due to the motion of an object, by using structural image data, which is described in detail below, may be applied to the aforementioned images.

Figures 10A, 10B:
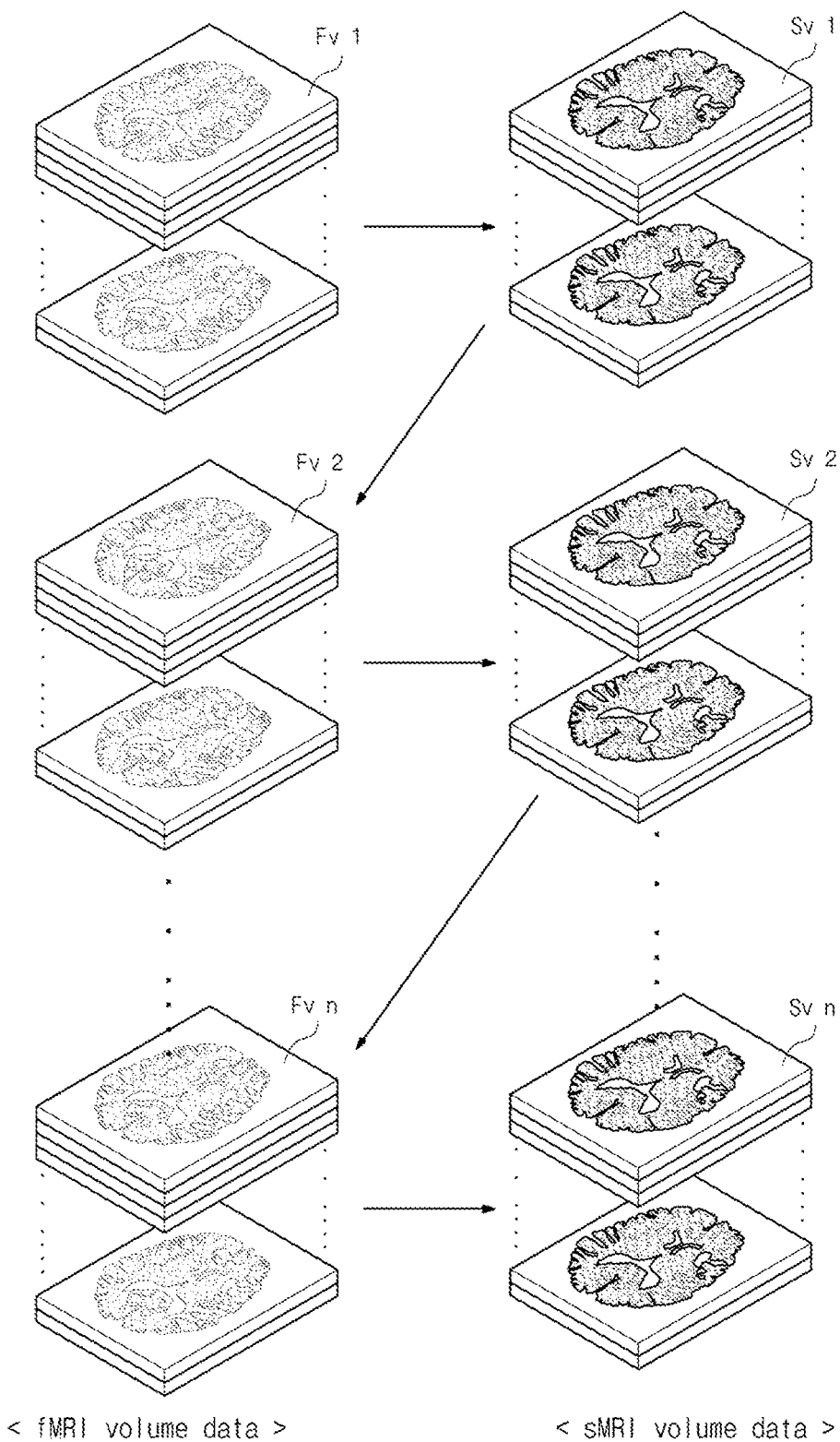
FIGS. 10A and 10B are views conceptually illustrating a method of acquiring structural image data of an object in relation to acquisition of functional image data, according to an exemplary embodiment.
Figure 11:
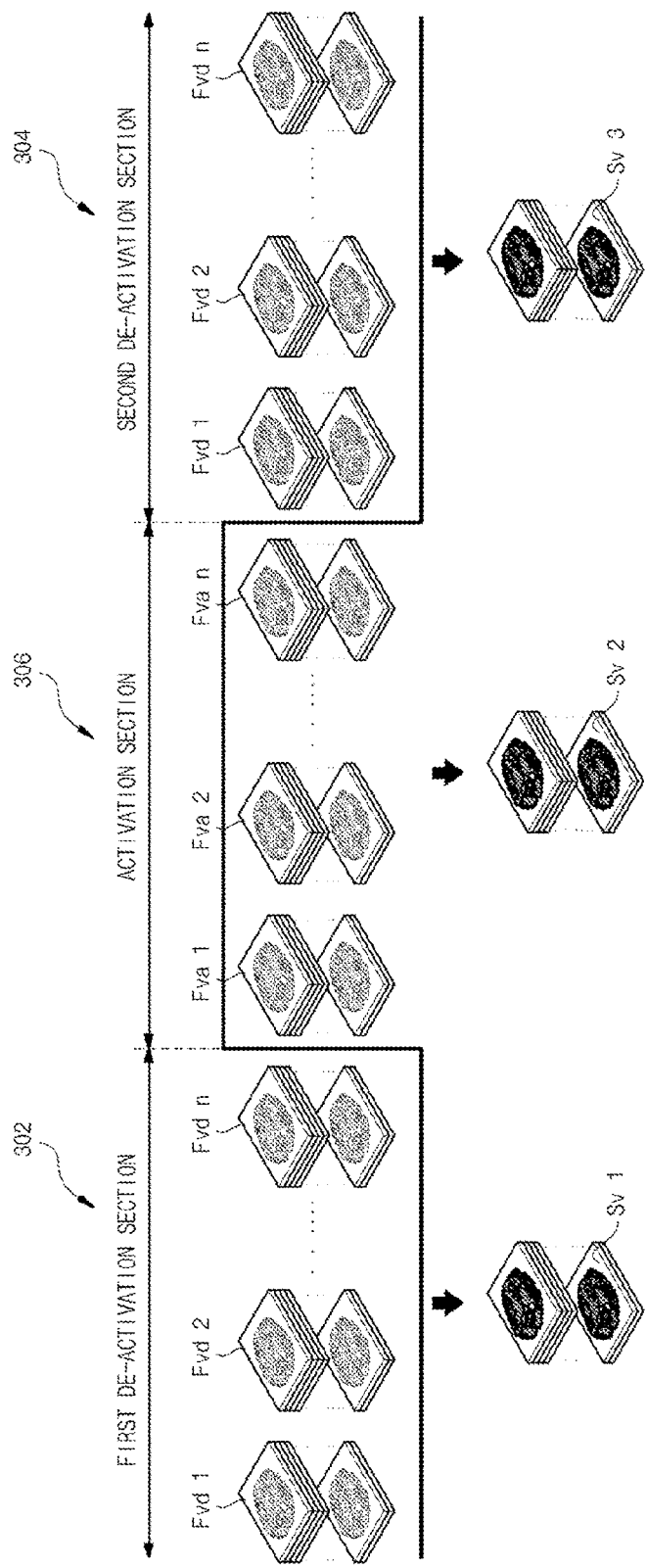
FIG. 11 is a view conceptually illustrating a method of acquiring structural image data of an object in relation to acquisition of functional image data, according to an exemplary embodiment.

FIGS. 9 to 11 are views conceptually illustrating various methods of acquiring structural image data in relation to acquisition of functional image data according to an exemplary embodiment.

FIG. 9A conceptually illustrates volume data of a functional image that is constituted of slices. FIG. 9B conceptually illustrates volume data of a structural image that is constituted of slices.

As illustrated in FIGS. 9A and 9B, the image processor 160 may acquire structural image data by acquiring slice data of volume data of a structural image whenever slice data of volume data of a functional image is acquired. That is, structural image data is acquired by alternately acquiring slice data of a functional image and slice data of a structural image.

In FIG. 9A, slice data of volume data of a functional image includes slices F1, F2, and F3 to Fn. In FIG. 9B, slice data of volume data of a structural image includes slices S1, S2, and S3 to Sn.

Arrows connecting the slice data represent an acquisition sequence of the slice data of the functional image and the slice data of the structural image.

As represented by the arrows, the functional slice data F1, the structural slice data S1, the functional slice data F2, the structural slice data S2, the functional slice data F3, and the structural slice data S3 are acquired in this order. As such, slice data of the structural image is acquired between the acquisitions of the respective slices of the functional image.

FIGS. 10A and 10B illustrate another method of acquiring structural image data.

FIG. 10A conceptually illustrates multiple volume data of a functional image, such as portions or slabs that are constituted of slices. FIG. 10B conceptually illustrates multiple volume data of a structural image, such as portions or slabs that are constituted of slices.

The image processor 160 may acquire structural image data by acquiring one volume data slab of a structural image whenever one volume data slab of a functional image is acquired. That is, structural image data is acquired by alternately acquiring volume data slabs of a functional image and the volume data slabs of a structural image.

In FIG. 10A, volume data slabs of a functional image include slabs Fv1 and Fv2 to Fvn. In FIG. 10B, volume data slabs of a structural image include slabs Sv1 and Sv2 to Svn.

Arrows connecting the respective volume data slabs represent an acquisition sequence of the volume data slabs of the functional image and the volume data slabs of the structural image.

As represented by the arrows, the functional volume data slab Fv1, the structural volume data slab Sv1, the functional volume data Fv2, the structural volume data slab Sv2, the functional volume data Fvn, and the structural volume data slab Svn are acquired in this order. As such, each of the volume data slabs of the structural image is acquired between the acquisitions of the respective volume data slabs of the functional image.

FIG. 11 illustrates another method of acquiring structural image data.

In FIG. 11, the sections for de-activation and activation of a specific function of interest to be confirmed via a functional image alternate with one another, as designated by a design-matrix for acquisition of the functional image.

For example, when attempting to confirm functional variation in the brain when an object views a particular image and when the object does not view the particular image, the case when the particular image is viewed corresponds to the activation section and the case when the particular image is not viewed corresponds to the de-activation section. Alternatively, when attempting to confirm functional difference in the brain when the object speaks and when the object does not speak, the case when the object speaks corresponds to the activation section, and the case when the object does not speak corresponds to the deactivation section.

Volume data of a functional image acquired in the first deactivation section 302 is designated by Fvd11, Fvd12, and Fvd1$n$, and volume data of a functional image acquired in the second deactivation section 304 is designated by Fvd21, Fvd22, and Fvd2$n$. Volume data of the functional image acquired in the activation section 306 is designated by Fva1, Fva2, and Fvan. Volume data of a structural image corresponding to the first deactivation section is designated by Sv1, corresponding to the activation section is designated by Sv2, and corresponding to the second deactivation section is designated by Sv3.

The image processor 160 may acquire multiple volume data slabs of a functional image in the activation section and the first and second deactivation sections.

Acquisition of structural image data illustrated in FIG. 11 is not carried out according to the slice data or the volume data slab of a functional image, as described above with reference to FIGS. 9 and 10, but is carried out according to the activation and deactivation sections in which multiple volume data slabs of a functional image are acquired.

The volume data slabs Sv1, Sv2, and Sv3 of a structural image are acquired one by one in each of the activation section and the first and second deactivation sections. Although FIG. 11 illustrates acquisition of one volume data slab of a structural image on a per section basis, an exemplary embodiment is not limited thereto, and more than one volume data slab of a structural image may be acquired in each of the activation and deactivation sections. Further, although FIG. 11 illustrates one activation section and two de-activation sections, the number of sections is not limited thereto.

When the structural image data is acquired by the method illustrated in FIG. 9 or FIG. 10, the volume data of a functional image and the volume data of a structural image correspond to each other in a ratio of 1 to 1, which ensures acquisition of more accurate information related to the motion of an object, from the structural image data.

When the structural image data is acquired by the method illustrated in FIG. 11, the volume data of a functional image and the volume data of a structural image correspond to each other in a ratio of n to 1, which reduces time for the acquisition of the structural image data, resulting in a reduced time for the acquisition of a functional image. That is, when correcting the functional image data by acquiring the structural image data via the methods of FIGS. 9 and 10, effects due to motion of an object may be more accurately corrected even if a longer time is taken. When correcting the functional image data by acquiring the structural image data via the method of FIG. 11, a time taken for acquisition of a functional image may be reduced, although the correction accuracy of the effects due to the motion of an object may be lower.

Accordingly, acquiring the structural image data by the method of FIG. 11 may be used when less motion of an object is expected, while acquiring the structural image data by the method of FIG. 9 or FIG. 10 may be used when a greater degree of motion of an object is expected.

As described above with reference to FIGS. 9 to 11, although structural image data may be acquired per slice data or volume data, or per activation section or deactivation section, this is only an example and an exemplary embodiment is not limited thereto. Slice data or volume data of a structural image may be acquired at a predefined time interval.

A method of improving an acquisition speed of structural image data is described in detail below with reference to FIGS. 12 to 16.

Figure 14A:
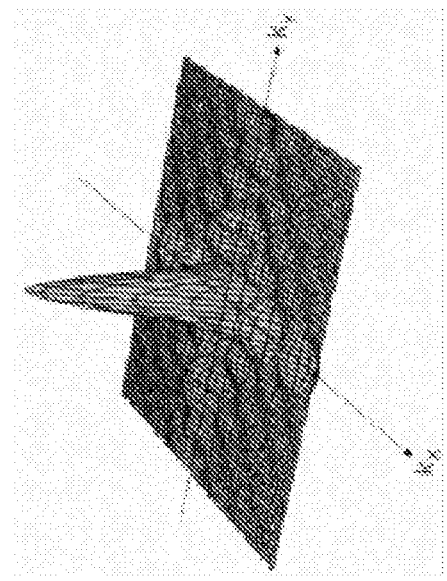
FIGS. 14A and 14B conceptually illustrate formation of a k-space via sampling of the entire echo signal.
Figure 14B:
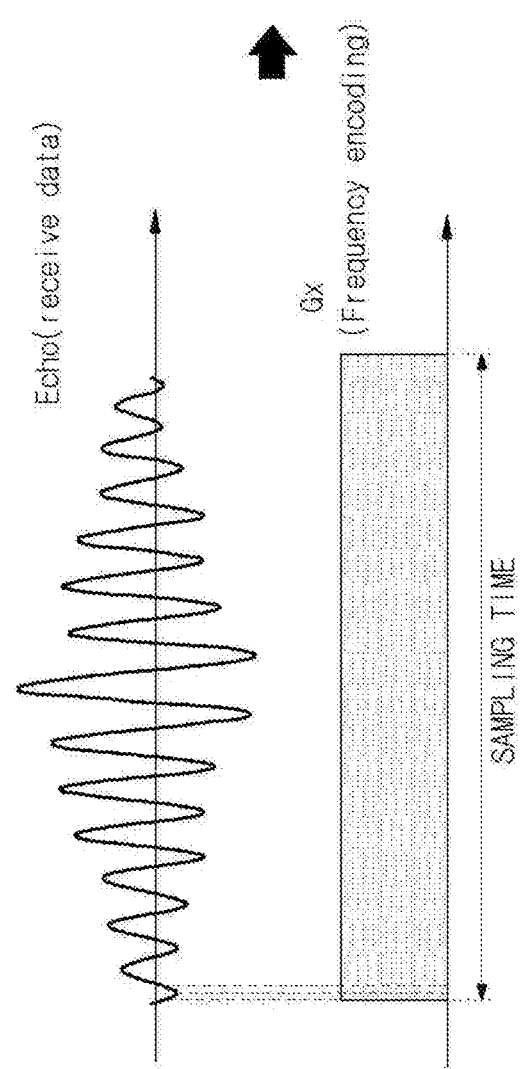

FIGS. 14A and 14B illustrate formation of a k-space via sampling of the entire echo signal. A 3D figure of the k-space formed by sampling the entire echo signal is conceptually illustrated in FIG. 14B, and a 2D figure of the k-space is illustrated, using graphs and images, in FIG. 16A.

Figure 16A:
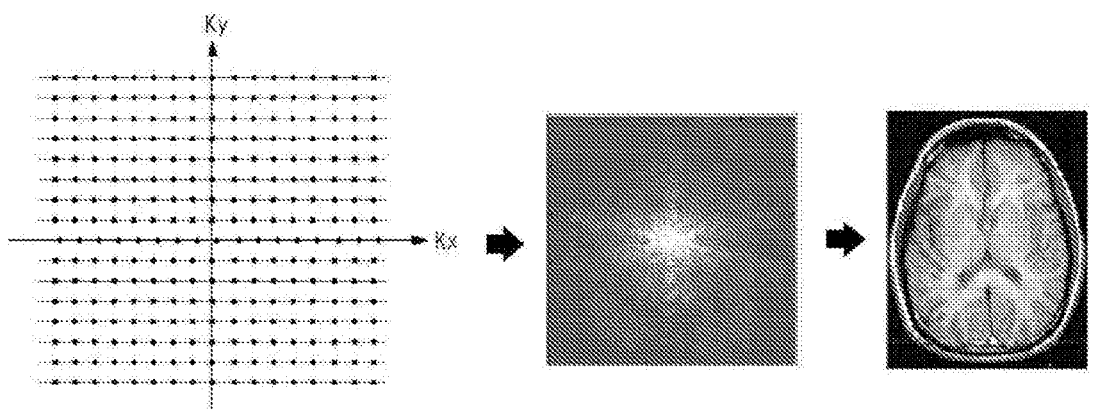
FIGS. 16A, 16B, and 16C are views comparing an image acquired from a k-space in which the entire echo signal is sampled with an image acquired from a k-space in which only low frequency regions are sampled.

FIG. 16A illustrates a functional MR image of the brain acquired from the k-space that is formed by sampling the entire echo signal.

Figure 15A:
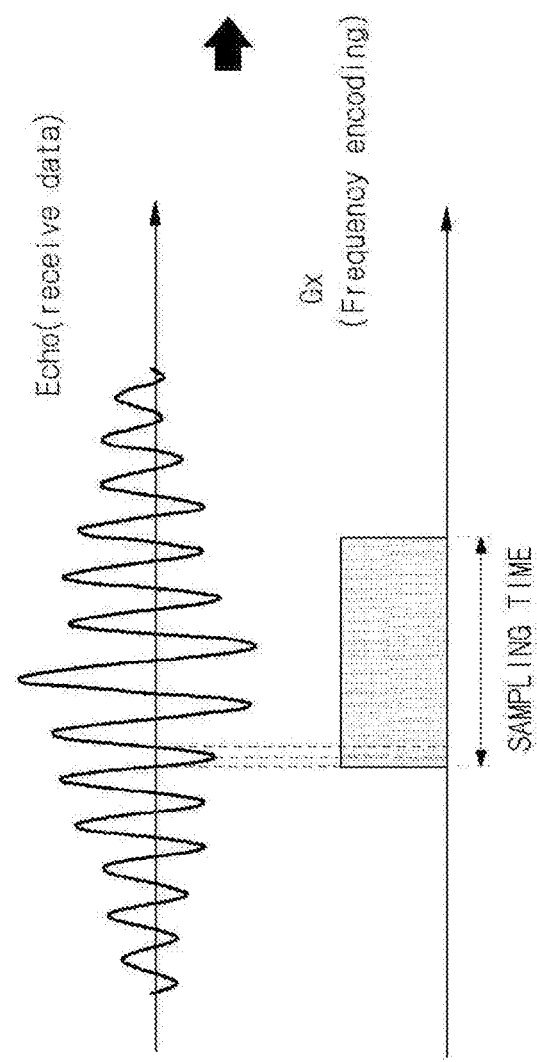
FIGS. 15A and 15B conceptually illustrate formation of a k-space via sampling of a low-frequency region of an echo signal.
Figure 15B:
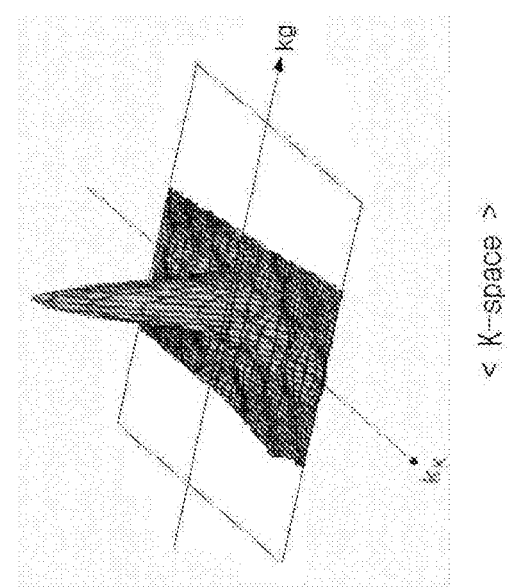
Figure 16B:
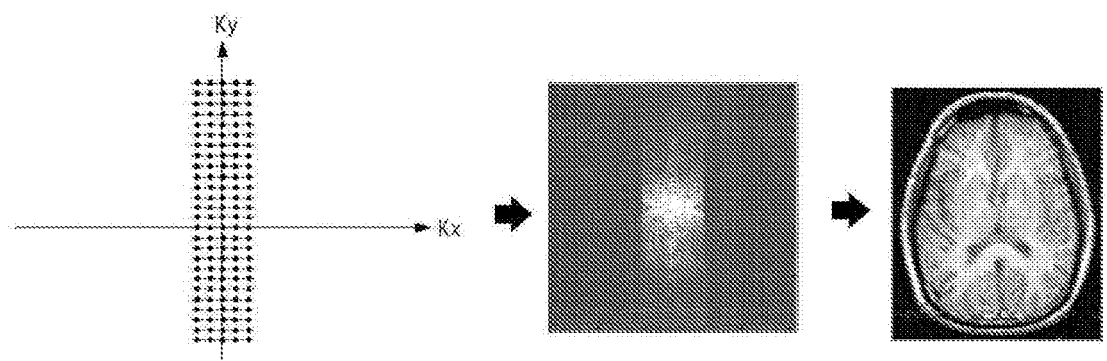

FIGS. 15A and 15B illustrate formation of a k-space via sampling of a low-frequency region corresponding to a center region of an echo signal. A 3D figure of the k-space formed by sampling the low-frequency region of the echo signal is conceptually illustrated in FIG. 15B, and a 2D figure of the k-space is illustrated, using graphs and images, in FIGS. 16B and 16C. FIG. 16B illustrates the k-space formed by sampling a wide low-frequency region of the echo signal, and FIG. 16C illustrates the k-space formed by sampling a narrow low-frequency region of the echo signal.

Figure 16C:
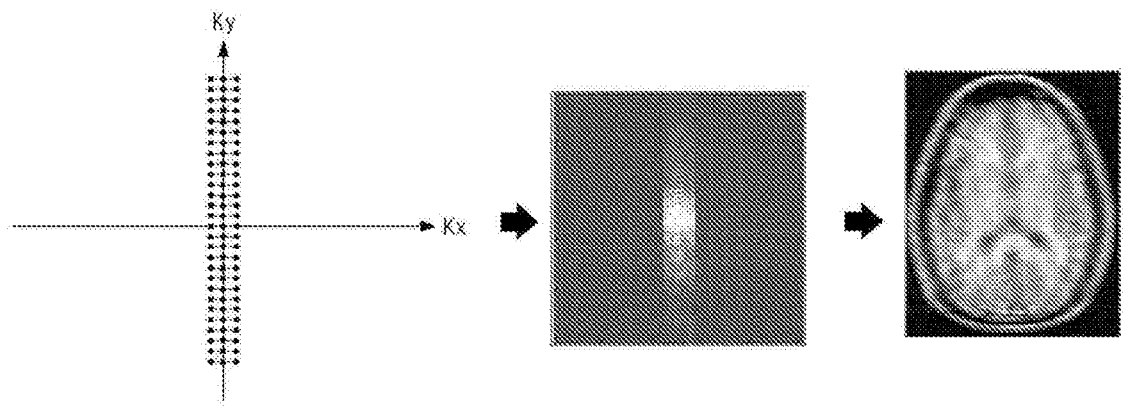

Comparing structural MR images acquired from the k-spaces illustrated in FIGS. 16A, 16B and 16C, the resolution of the structural MR image acquired by sampling the entire echo signal of FIG. 16A is superior to the resolution of the image of FIG. 16B or 16C. The resolution of the structural MR image of FIG. 16B is superior to the resolution of the image of FIG. 16C. However, these images have no substantial difference in contrast.

Structural image data is used to calculate information related to the motion of an object, and, thus, may require contrast suitable to simply recognize motion of the object. Accordingly, although structural image data may be acquired from the k-space formed by sampling the entire echo signal as illustrated in FIG. 16A, to achieve more rapid acquisition of structural image data, structural image data may be acquired from the k-space formed by sampling the low-frequency region of the echo signal, as illustrated in FIGS. 16B and 16C.

Figure 12:
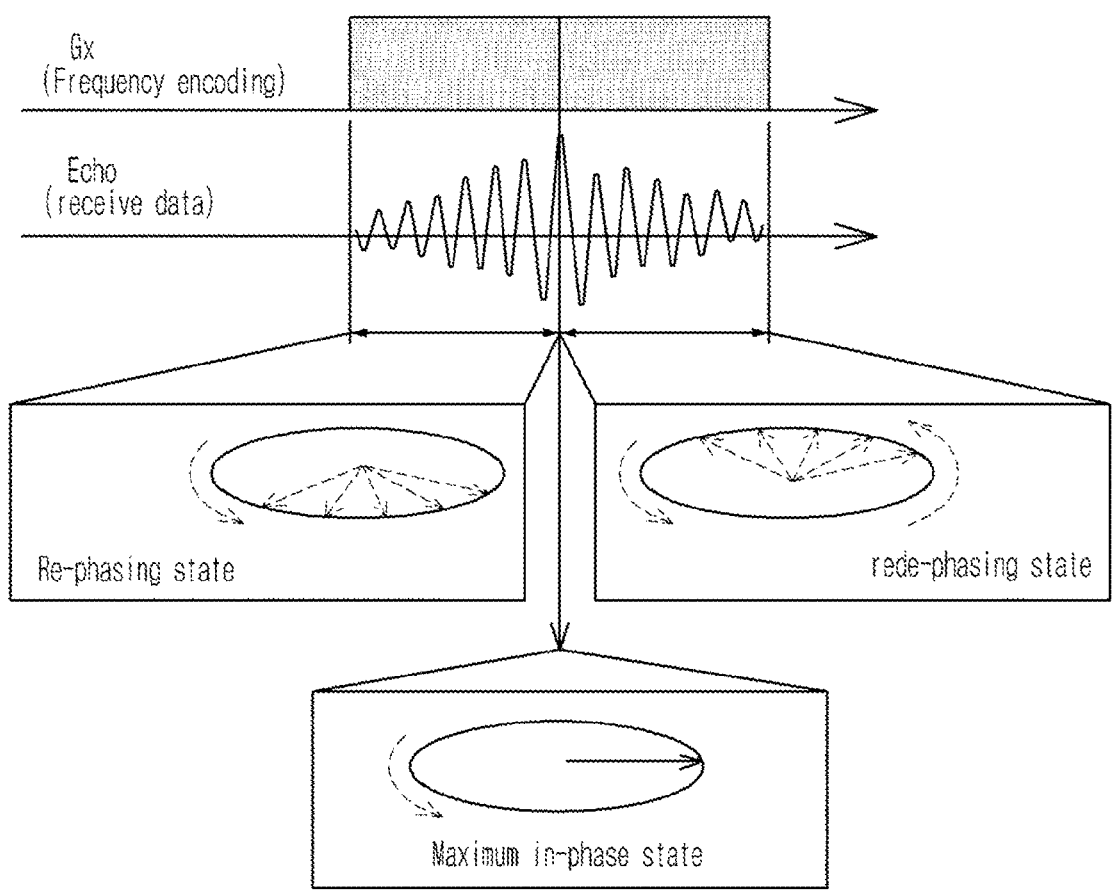
FIG. 12 is a view of the center of a k-space in relation to the frequency encoding of echo signals.
Figure 13:
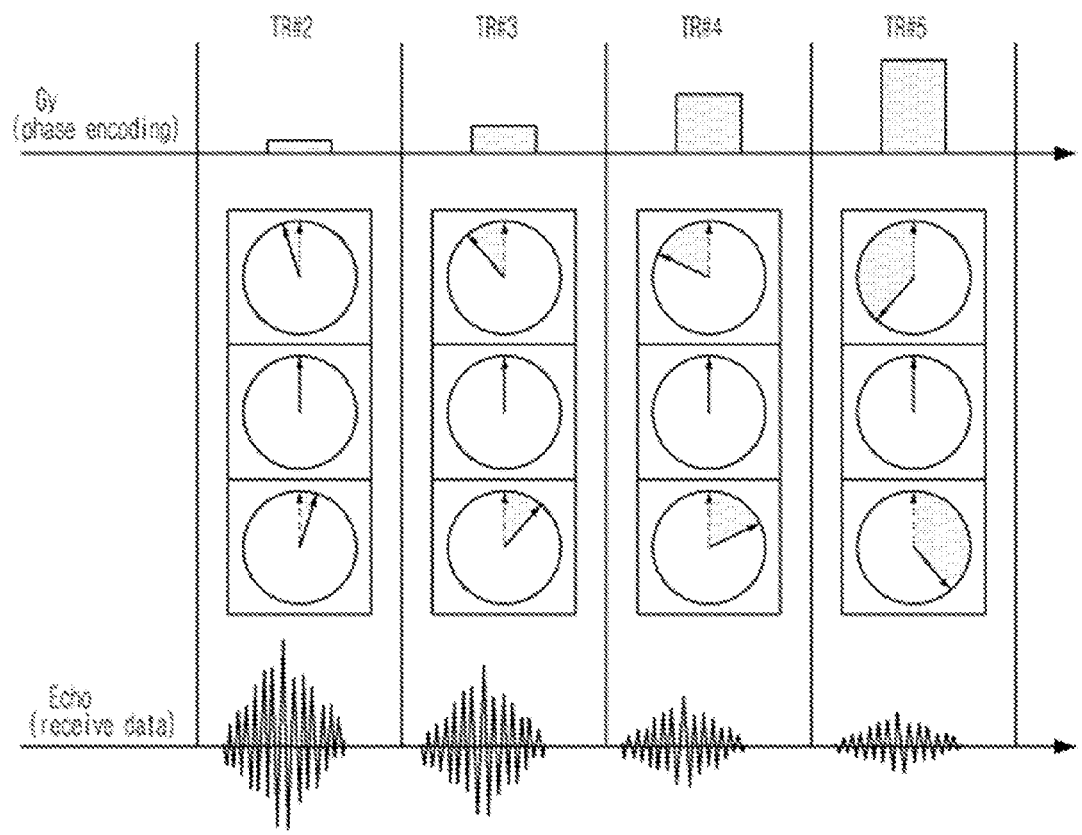
FIG. 13 is a view of the center of a k-space in relation to the phase encoding of echo signals.

In general, data located in the center of the k-space determines the contrast of an image and the strength of a signal. This is because the data located in the center of the k-space is data in phase owing to focusing of spins during frequency encoding differently from the surrounding area as illustrated in FIG. 12. This data also experiences no or less phase shift during phase encoding as illustrated in FIG. 13. As appreciated from FIG. 13, an echo signal acquired at a small TR number is located in the center of the k-space, and, for example, a degree of phase shift is low at TR#2.

For this reason, to achieve more rapid acquisition of structural image data, the k-space is formed by sampling the low-frequency region as the center region of the echo signal that determines the contrast of an image and the strength of the signal and, thus, may have a dominant effect on image reconstruction.

Although FIGS. 16A, 16B, and 16C illustrate an orthographic k-space formed by sampling an echo signal using orthogonal coordinates, an exemplary embodiment is not limited thereto. Structural image data may be acquired from a k-space formed via radial trajectory sampling or spiral sampling.

As described above, an acquisition speed of structural image data may be improved as a result of forming the k-space by sampling the low-frequency region of the echo signal. Acquisition speed of structural image data may be also be improved by sampling the echo signal via compressed sensing.

Sampling is carried out to convert an analog signal into a digital signal, and accurate recovery of a signal may be possible using samples taken at the Nyquist rate of twice the highest frequency present in the signal of interest.

The compressed sensing proposes a method of recovering a signal even without samples taken at the Nyquist rate or more, i.e., a method of recovering an original signal via sub-Nyquist sampling. This method is based on the assumed presence of so-called sparse signals as typical signals, which mostly have values of zero when transformed into a particular signal space.

A sparse signal is a signal whose y values at most x values are zeroes and y values at a relatively small number of x values are non-zero values when drawn on an X-Y plot. With the theory of compressed sensing, a sparse signal may be recovered even via a small number of linear measurements.

Accordingly, since compressed sensing enables speedy signal sampling, acquiring structural image data by sampling an echo signal via compressed sensing may reduce data acquisition time.

Compressed sensing is a sampling method known to those skilled in the art, and thus a detailed description thereof is omitted.

As described above, to reduce time for acquisition of structural image data, a k-space may be formed by sampling a low-frequency region of an echo signal or by sampling an echo signal via compressed sensing.

Figure 17:
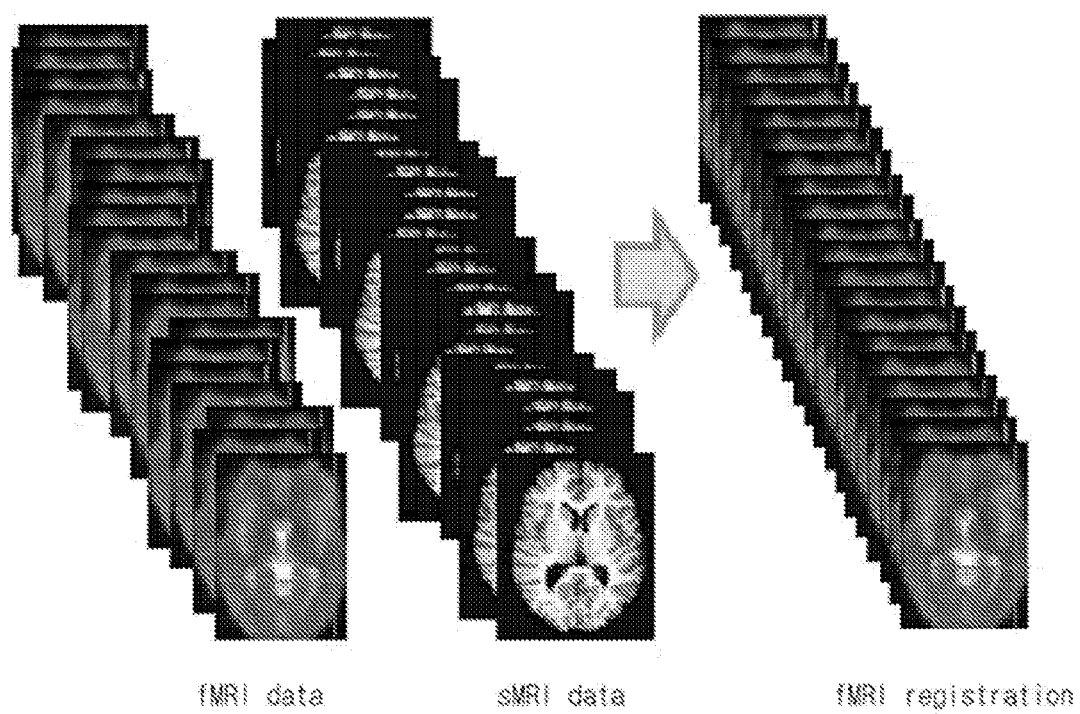
FIG. 17 is a view conceptually illustrating a procedure of correcting artifacts of a functional image caused by motion of an object using a structural image.

FIG. 17 is a view conceptually illustrating a procedure of acquiring information related to motion of an object based on structural image data, and acquiring a functional image whose artifacts caused by motion of an object are corrected via registration of functional image data based on the acquired information.

If structural image data is acquired, the image processor 160 acquires a structural image via the described-above rigid body registration of structural image data.

The image processor 160 calculates a transformation matrix used in the registration of structural image data, and uses the transformation matrix for registration of functional image data.

As described above, functional image data is unsuitable for correction of effects due to motion of an object based on anatomical information of the functional image data. Therefore, the transformation matrix is calculated from the registration of structural image data that clearly reveals an anatomical structure.

Since structural image data clearly reveals an anatomical structure of an object's organ and the transformation matrix used to register structural image data is also used to register functional image data, it may be possible to remove effects due to motion of the object revealed in functional image data.

Figure 18:
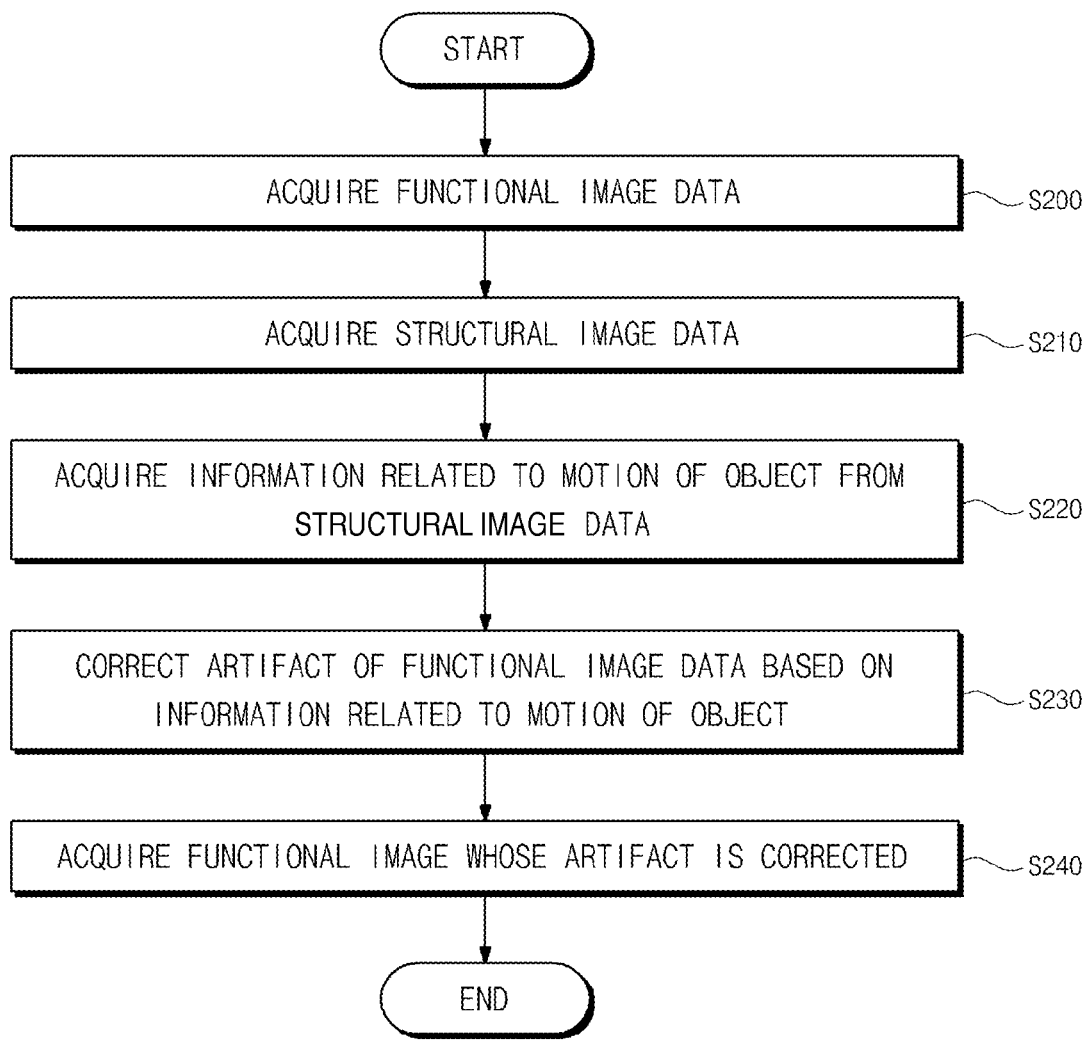
FIG. 18 is a flowchart illustrating a method of acquiring a functional image according to an exemplary embodiment.

FIG. 18 is a flowchart illustrating a method of acquiring a functional image using the MRI apparatus according to an exemplary embodiment.

Referring to FIG. 18, functional image data and structural image data with respect to an object are acquired (operations S200 and S210).

Various methods of acquiring structural image data in relation to acquisition of functional image data are described above with reference to FIGS. 9 to 11.

Figure 19:
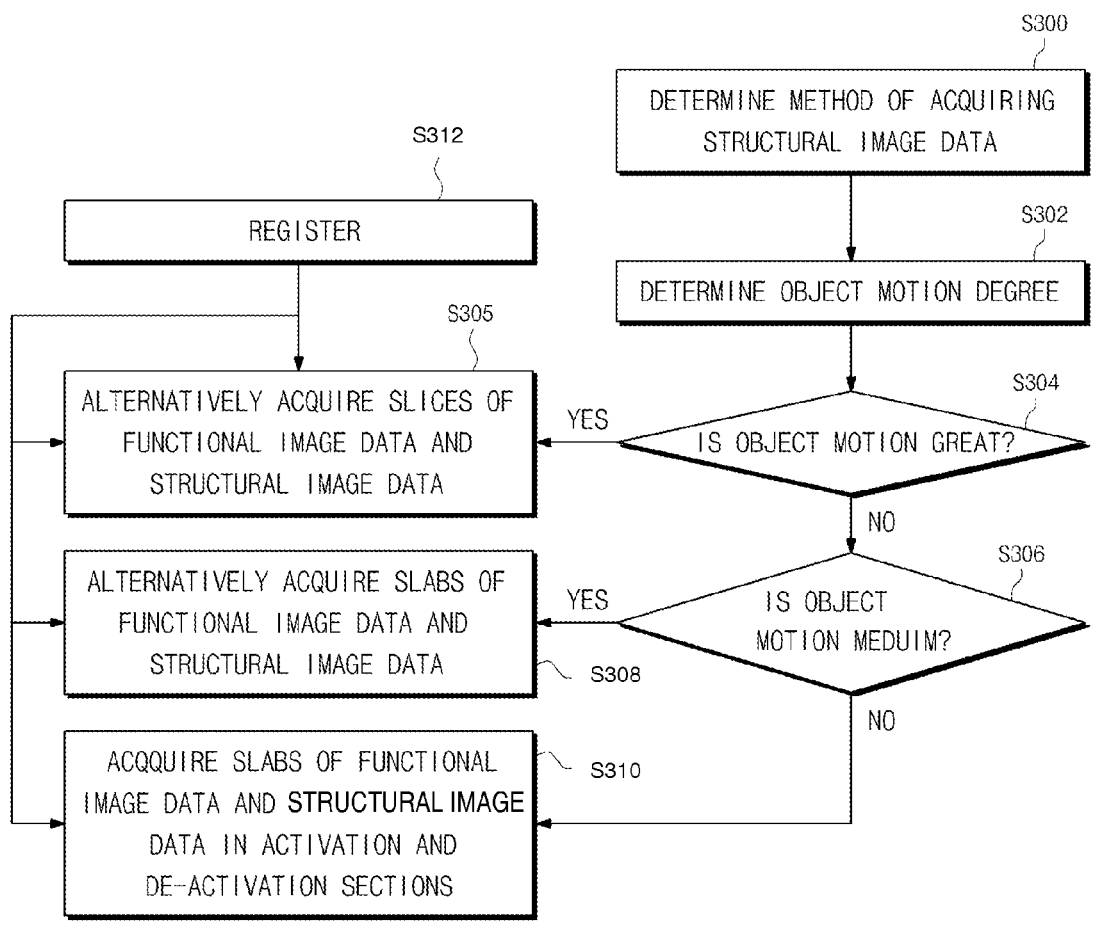
FIG. 19 is a flowchart of acquiring a functional image according to an exemplary embodiment.

With reference to FIG. 19, the image processor 160 may determine the method to acquire the structural image data (operation S300). For example, the method may be a method described with reference to FIGS. 9-11 and may be determined based on expected degree of the object motion, image quality objectives, time constraints of imaging, etc.

In operation S302, the image processor 160 may determine whether a degree of the object motion is expected to be greater or lower. For example, if an object is a child or an animal, a degree of motion may be expected to be greater.

The image processor 160 may classify the degree of motion into, for example, the great, medium, and low levels. Alternatively, a degree of object motion may be determined at the pre-examination stage by examining the previous records of the object or estimating the object motion with a sensor.

In operation S304, it may be determined that the expected object motion is great, and the image processor 160 may determine the method to acquire the structural image data according to an exemplary embodiment described above with reference to FIG. 9. This determination may be also made when the image processor 160 determines that an image of a higher quality is desired and/or when there is no great time constraints with respect to image acquisition. That is, the structural image data is acquired by alternately acquiring the slice data of a functional image and the slice data of a structural image (operation S305).

In operation S306, if it is determined that the expected object motion is medium, the image processor 160 may determine the method to acquire the structural image data according to an exemplary embodiment described above with reference to FIG. 10. This determination may be also made when the image processor 160 determines that an image of a lower quality is acceptable and/or there is a time constraint with respect to image acquisition.

In operation S308, the image processor 160 may acquire structural image data by acquiring one volume data slab of a structural image whenever one volume data slab of a functional image is acquired. That is, structural image data is acquired by alternately acquiring volume data slab of a functional image and volume data slab of a structural image.

In operation S306, if it is determined that the expected object motion is low, the image processor 160 may determine the method to acquire the structural image data according to an exemplary embodiment described above with reference to FIG. 11. This determination may be also made when the image processor 160 determines that an image of a lower quality is acceptable and when there is great time constraints with respect to image acquisition.

In operation S310, the image processor 160 may acquire multiple volume data slabs of a functional image in the activation section and each of respective volume data slabs in the deactivation section.

Also, as illustrated in FIG. 19, the image processor 160 may perform the registration prior to or during acquiring the structural image data, by using, for example, a rigid registration (operation S312). Further, some operations described above with reference to FIG. 19 may be omitted, and the image processor 160 may determine the method to proceed based on the pre-stored criteria or on a user selection, in operation S300.

A method of improving an acquisition speed of structural image data is described above with reference to FIGS. 12 to 16 and is not repeated.

With reference again to FIG. 18, if the structural image data is acquired, information related to the motion of the object is acquired from the acquired structural image data (operation S220).

Acquiring information related to the motion of an object based on structural image data, and acquiring a functional image whose artifacts caused by motion of an object are corrected via registration of functional image data based on the acquired information is described above in detail with reference to FIG. 17.

Figure 20:
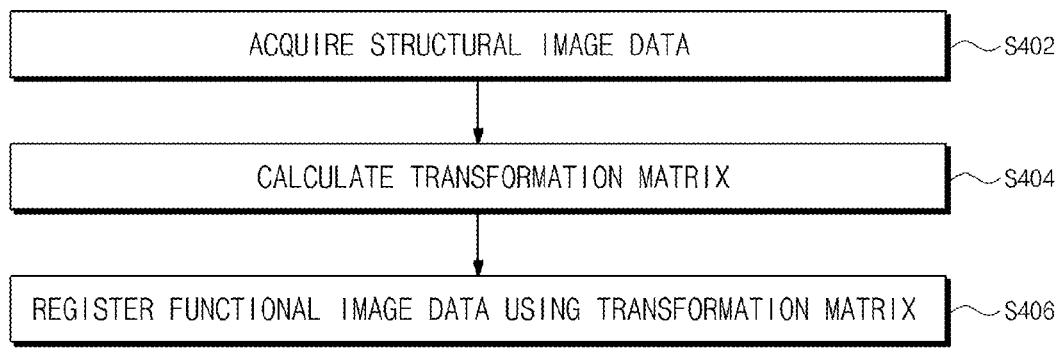
FIG. 20 is a flowchart of acquiring a functional image according to an exemplary embodiment.

With reference to FIG. 20, the pieces of structural image data are acquired, and the image processor 160 acquires a structural image by using the rigid body registration of the structural image data, in operation S402.

In operation S404, the image processor 160 calculates a transformation matrix used in the registration of structural image data.

In operation S406, the image processor 160 registers the functional image data based on the transformation matrix used in the registration of the structural image data.

As described above, the functional image data may be unsuitable for correction of effects due to the motion of an object based on anatomical information of the functional image data. Therefore, the transformation matrix is calculated by using the registration of the structural image data that clearly reveals an anatomical structure.

That is, information related to motion of the object calculated via the structural image data is represented as the transformation matrix used in the registration of the structural image data.

With reference again to FIG. 18, when the information related to motion of the object is calculated, artifacts of the functional image data are corrected based on the information (operation S230), and a functional image whose artifacts are corrected is acquired (operation S240).

Thus, the transformation matrix used in registration of the structural image data is calculated, and the image processor 160 performs a registration of the functional image data by using the calculated transformation matrix.

Since the transformation matrix is calculated based on the structural image data that clearly shows an anatomical structure, registering the functional image data using the transformation matrix enables correction of artifacts due to the motion of the object.

Thus, the display displays a functional image whose artifacts are corrected via registration of the functional image data.

As is apparent from the above description, according to an aspect of an exemplary embodiment, information related to motion of an object may be more accurately acquired, which enables more accurate correction of artifacts due to motion of the object.

Further, statistical accuracy and reliability may be improved upon analysis of functional images.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of acquiring a functional image by a magnetic resonance imaging (MRI) apparatus, the method comprising:
   acquiring functional image data of an object that measures brain functionalities by detecting associated changes in a blood flow;
   acquiring structural image data of the object that represents an anatomical structure of the brain;
   registering the structural image data;
   determining registration information of the structural image data;
   correcting the functional image data for motion of the object by registering the functional image data based on the registration information of the structural image data; and
   obtaining a functional image of the object,
   wherein the structural image data are acquired in correspondence with an acquisition of corresponding functional image data, and
   the acquiring the structural image data includes acquiring the structural image data between acquisitions of respective functional image data.

2. The method according to claim 1, wherein the functional image includes a brain functional image.

3. The method according to claim 1, wherein the acquiring the structural image data includes acquiring the structural image data at time intervals.

4. The method according to claim 1, wherein the functional image data include slice image data, and
   the structural image data include slice image data.

5. The method according to claim 1, wherein the functional image data include volume image data slabs, and
the structural image data include volume image data slabs.

6. The method according to claim 1, wherein the acquiring the structural image data includes acquiring the structural image data in each of an activation section and a deactivation section of a function of interest.

7. The method according to claim 1, wherein the acquiring the structural image data includes:
forming a k-space by sampling an echo signal of the object via compressed sensing; and
acquiring the structural image data from the k-space.

8. The method according to claim 1, wherein the acquiring the structural image data includes:
forming a k-space by sampling a low-frequency region of an echo signal of the object; and
acquiring the structural image data from the k-space.

9. The method according to claim 1, wherein the
registering the structural image data includes
calculating a transformation matrix used in the registering the structural image data.

10. The method according to claim 9, wherein the obtaining the functional image includes:
obtaining the functional image whose artifacts due to the motion of the object are corrected by registering the functional image data based on the transformation matrix.

11. A magnetic resonance imaging (MRI) apparatus comprising:
an image processor that acquires functional image data which measures brain functionalities by detecting associated changes in a blood flow and structural image data which represents an anatomical structure of the brain of an object, acquires structural image data of the object that represents an anatomical structure of the brain, registers the structural image data, determines registration information of the structural image data, corrects the functional image data for motion of the object by registering the functional image data based on the registration information of the structural image data, and acquires a functional image of the object; and
a display that displays the functional image,
wherein the image processor acquires the structural image data in correspondence with an acquisition of corresponding functional image data, and
the structural image data are acquired between acquisitions of respective functional image data.

12. The apparatus according to claim 11, wherein the image processor acquires the structural image data at time intervals.

13. The apparatus according to claim 11, wherein the functional image data include slice image data, and
the structural image data include slice image data.

14. The apparatus according to claim 11, wherein the functional image data include volume image data, and
the structural image data include volume image data.

15. The apparatus according to claim 11, wherein the image processor acquires the structural image data in each of an activation section and a deactivation section of a function of interest.

16. The apparatus according to claim 11, wherein the image processor forms a k-space by sampling an echo signal of the object via compressed sensing, and
acquires the structural image data from the k-space.

17. The apparatus according to claim 11, wherein the image processor forms a k-space by sampling a low-frequency region of an echo signal of the object, and
acquires the structural image data from the k-space.

18. The apparatus according to claim 11, wherein the image processor
calculates a transformation matrix used in a registration of the structural image data, and
acquires the functional image whose artifacts due to the motion of the object are corrected, by registering the functional image data based on the transformation matrix.

19. A magnetic resonance imaging (MRI) method comprising:
acquiring, substantially contemporaneously, pieces of functional image data which measures brain functionalities by detecting associated changes in a blood flow and pieces of structural image data which represents an anatomical structure of the brain, of an object;
registering the structural image data and acquiring transformation parameters of the pieces of the structural image data with respect to an object motion;
correcting the pieces of the functional image data for the object motion, by registering the pieces of functional image data using the transformation parameters of the pieces of the structural image data; and
obtaining a functional image of the object,
wherein the pieces of the structural image data are acquired in correspondence with an acquisition of corresponding pieces of functional image data, and
the acquiring the structural image data includes acquiring the pieces of the structural image data between acquisitions of respective pieces of the functional image data.

20. The method according to claim 19, wherein the functional image includes a brain functional image.

21. The method according to claim 19, wherein the acquiring the pieces of the functional image data and the pieces of the structural image data comprises one of:
acquiring slices of the functional image data alternatively with acquiring respective slices of the structural image data,
acquiring slabs of the functional image data alternatively with acquiring respective slabs of the structural image data, and
acquiring multiple slabs of the functional image data and acquiring one respective slab of the structural image data.

22. The method according to claim 19, wherein the acquiring the transformation parameters comprises:
calculating a transformation matrix of the acquired pieces of the structural image data.

23. The method according to claim 22, wherein the correcting comprises:
registering the functional image data based on the transformation matrix; and
correcting artifacts due to the object motion.

24. The method according to claim 1, wherein the acquiring the functional image data and the acquiring the structural data include sequentially interleaving acquisitions of the structural image data with the acquisitions of the corresponding functional image data.

* * * * *